(12) United States Patent
Edwards et al.

(10) Patent No.: US 11,213,312 B2
(45) Date of Patent: Jan. 4, 2022

(54) METHODS OF RECIPROCATION IN A SURGICAL SHAVER

(71) Applicant: Gyrus ACMI, Inc., Southborough, MA (US)

(72) Inventors: Kevin Edwards, Olive Branch, MS (US); Ahmad Alsaffar, Bartlett, TN (US); Joel Willhite, Memphis, TN (US); David Church, Millington, TN (US); Daniel Goldberg, Germantown, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 0 days.

(21) Appl. No.: 16/286,748

(22) Filed: Feb. 27, 2019

(65) Prior Publication Data

US 2020/0268401 A1 Aug. 27, 2020

(51) Int. Cl.
*A61B 17/32* (2006.01)
*A61B 17/16* (2006.01)
*A61B 17/3207* (2006.01)

(52) U.S. Cl.
CPC .... *A61B 17/32002* (2013.01); *A61B 17/1624* (2013.01); *A61B 17/1628* (2013.01); *A61B 17/1659* (2013.01); *A61B 17/320758* (2013.01); *A61B 2017/320028* (2013.01); *A61B 2017/320032* (2013.01)

(58) Field of Classification Search
CPC .. A61B 17/32002; A61B 2017/320008; A61B 2017/32004; A61B 2017/320064; A61B 17/1635; A61B 17/1604; A61B 17/1608; A61B 17/1611
See application file for complete search history.

(56) References Cited

U.S. PATENT DOCUMENTS

| 4,940,468 | A | 7/1990 | Petillo |
| 6,156,049 | A | 12/2000 | Lovato et al. |
| 6,258,111 | B1 | 7/2001 | Ross et al. |
| 6,342,061 | B1 * | 1/2002 | Kauker ............ A61B 17/32002 606/180 |
| 11,141,182 | B2 | 10/2021 | Goldberg et al. |

(Continued)

FOREIGN PATENT DOCUMENTS

| EP | 3698737 A1 | 8/2020 |
| JP | 2005507703 A | 3/2005 |
| JP | 2017529940 A | 10/2017 |

OTHER PUBLICATIONS

Wikipedia contributors. "Scotch yoke," Wikipedia, The Free Encyclopedia. Wikipedia, The Free Encyclopedia, Apr. 1, 2019. Web. May 29, 2019, 3 pages.

(Continued)

*Primary Examiner* — Kevin T Truong
*Assistant Examiner* — Lisa Nguyen
(74) *Attorney, Agent, or Firm* — Schwegman Lundberg & Woessner, P.A.

(57) ABSTRACT

Disclosed herein is a medical device. The medical device includes a blade tube section, a motor, and a mechanical arrangement. The blade tube section includes an outer blade tube, inner blade tube, and a cutting window at a distal end of the blade tube section. The motor is offset from a central axis of the blade tube section. The mechanical arrangement is between the inner blade tube and the motor.

10 Claims, 5 Drawing Sheets

(56) References Cited

U.S. PATENT DOCUMENTS

| | | | |
|---|---|---|---|
| 11,147,579 | B2 | 10/2021 | Edwards et al. |
| 2002/0183851 | A1* | 12/2002 | Spiegelberg .......... A61F 2/4607 623/22.12 |
| 2003/0009888 | A1 | 1/2003 | Marinkovich et al. |
| 2003/0083684 | A1* | 5/2003 | Cesarini ........... A61B 17/32002 606/170 |
| 2005/0005458 | A1 | 1/2005 | Marinkovich et al. |
| 2007/0282344 | A1* | 12/2007 | Yedlicka ............ A61B 17/1624 606/80 |
| 2009/0270893 | A1 | 10/2009 | Arcenio |
| 2011/0028898 | A1 | 2/2011 | Clark, III et al. |
| 2011/0247847 | A1 | 10/2011 | Holmes et al. |
| 2013/0211321 | A1 | 8/2013 | Dubois et al. |
| 2015/0090058 | A1 | 4/2015 | Roschke et al. |
| 2016/0331645 | A1 | 11/2016 | Bagwell et al. |
| 2017/0231654 | A1 | 8/2017 | Cesarini et al. |
| 2018/0146974 | A1 | 5/2018 | Bjursten |
| 2019/0070215 | A1* | 3/2019 | Perry ................. A61B 17/3421 |
| 2020/0268400 | A1 | 8/2020 | Edwards et al. |
| 2020/0268402 | A1 | 8/2020 | Edwards et al. |
| 2020/0268946 | A1* | 8/2020 | Wood ............... A61B 17/32002 |
| 2020/0275944 | A1 | 9/2020 | Goldberg et al. |

OTHER PUBLICATIONS

Wikipedia contributors. "Driving wheel." Wikipedia, The Free Encyclopedia. Wikipedia, The Free Encyclopedia, Apr. 4, 2019. Web. May 22, 2019, 4 pages.

"U.S. Appl. No. 16/290,047, Non Final Office Action dated Jun. 16, 2020", 13 pgs.

"European Application Serial No. 20158861.3, Extended European Search Report dated Jun. 29, 2020", 7 pgs.

"U.S. Appl. No. 16/282,505, Response filed Jan. 28, 2021 to Non Final Office Action dated Oct. 28, 2020", 11 pgs.

"U.S. Appl. No. 16/287,329, Response filed Feb. 22, 2021 to Non Final Office Action dated Nov. 20, 2020", 12 pgs.

"U.S. Appl. No. 16/290,047, Advisory Action dated Jan. 8, 2021", 3 pgs.

"U.S. Appl. No. 16/290,047, Response filed Jan. 15, 2021 to Advisory Action dated Jan. 8, 2021", 10 pgs.

U.S. Appl. No. 16/290,047, filed Mar. 1, 2019, Methods of Reciprocation in a Surgical Shaver (as amended).

U.S. Appl. No. 16/287,329, filed Feb. 27, 2019, Methods of Reciprocation in a Surgical Shaver.

U.S. Appl. No. 16/282,505, filed Feb. 22, 2019, Methods of Reciprocation in a Surgical Shaver.

"U.S. Appl. No. 16/282,505, Non Final Office Action dated Oct. 28, 2020", 13 pgs.

"U.S. Appl. No. 16/287,329, Non Final Office Action dated Nov. 20, 2020", 14 pgs.

"U.S. Appl. No. 16/290,047, Final Office Action dated Oct. 20, 2020", 11 pgs.

"U.S. Appl. No. 16/290,047, Response filed Sep. 16, 2020 to Non Final Office Action dated Jun. 16, 2020", 10 pgs.

"U.S. Appl. No. 16/290,047, Response filed Dec. 10, 2020 to Final Office Action dated Oct. 20, 2020", 9 pgs.

"U.S. Appl. No. 16/282,505, Non Final Office Action dated Apr. 30, 2021", 11 pgs.

"U.S. Appl. No. 16/287,329, Corrected Notice of Allowability dated Jun. 21, 2021", 2 pgs.

"U.S. Appl. No. 16/287,329, Notice of Allowance dated Jun. 11, 2021", 8 pgs.

"U.S. Appl. No. 16/290,047, Corrected Notice of Allowability dated Jun. 30, 2021", 3 pgs.

"U.S. Appl. No. 16/290,047, Corrected Notice of Allowability dated Jul. 12, 2021", 2 pgs.

"U.S. Appl. No. 16/290,047, Notice of Allowance dated Jun. 23, 2021", 6 pgs.

"European Application Serial No. 20158861.3, Response filed Feb. 25, 2021 to Extended European Search Report dated Jun. 29, 2020", 9 pgs.

"Japanese Application Serial No. 2020-28522, Response filed Jun. 15, 2021 to Office Action dated Mar. 15, 2021", with English translation of claims, 7 pgs.

"Japanese Application Serial No. 2020-28552, Notification of Reasons for Refusal dated Mar. 15, 2021", with English translation, 14 pgs.

"U.S. Appl. No. 16/282,505, Response filed Jul. 30, 2021 to Non Final Office Action dated Apr. 30, 2021", 10 pgs.

"Japanese Application Serial No. 2020-028552, Final Notification of Reasons for Refusal dated Aug. 23, 2021", w/ English Translation, 4 pgs.

"U.S. Appl. No. 16/282,505, Final Office Action dated Oct. 25, 2021", 17 pgs.

"U.S. Appl. No. 16/287,329, Corrected Notice of Allowability dated Sep. 15, 2021", 2 pgs.

"U.S. Appl. No. 16/290,047, Corrected Notice of Allowability dated Sep. 16, 2021", 2 pgs.

* cited by examiner

METHODS OF RECIPROCATION IN A SURGICAL SHAVER

BACKGROUND

Field of the Invention

The invention relates to a medical device and more specifically relates to methods of reciprocation for a surgical shaver device.

Brief Description of Prior Developments

Conventional surgical shavers generally use a rotational motor coupled with a parallel gear train to impart oscillatory motion on the shaver blades. However, using the oscillating motion to cut can tear and strip mucosa. Reciprocating blades, on the other hand, can create cleaner, more precise cuts.

Reciprocating surgical shavers exist in the market, however these devices generally use air pressure from a vacuum to drive the reciprocation, which can result in a weak cutting stroke and in turn make the device unable to cut through the tissue necessary to complete a procedure.

Accordingly, there is a need to provide improved and reliable medical device configurations having reciprocating blades.

SUMMARY

In accordance with one aspect of the invention, a medical device is disclosed. The medical device includes a blade tube section, a motor, and a mechanical arrangement. The blade tube section includes an outer blade tube, inner blade tube, and a cutting window at a distal end of the blade tube section. The motor is offset from a central axis of the blade tube section. The mechanical arrangement is between the inner blade tube and the motor.

In accordance with another aspect of the invention, a medical device is disclosed. The medical device includes a blade tube section, a motor, and a cam portion. The blade tube section includes an outer blade tube, an inner blade tube, and a cutting window at a distal end of the blade tube section. The cam portion is between the inner blade tube and the motor.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
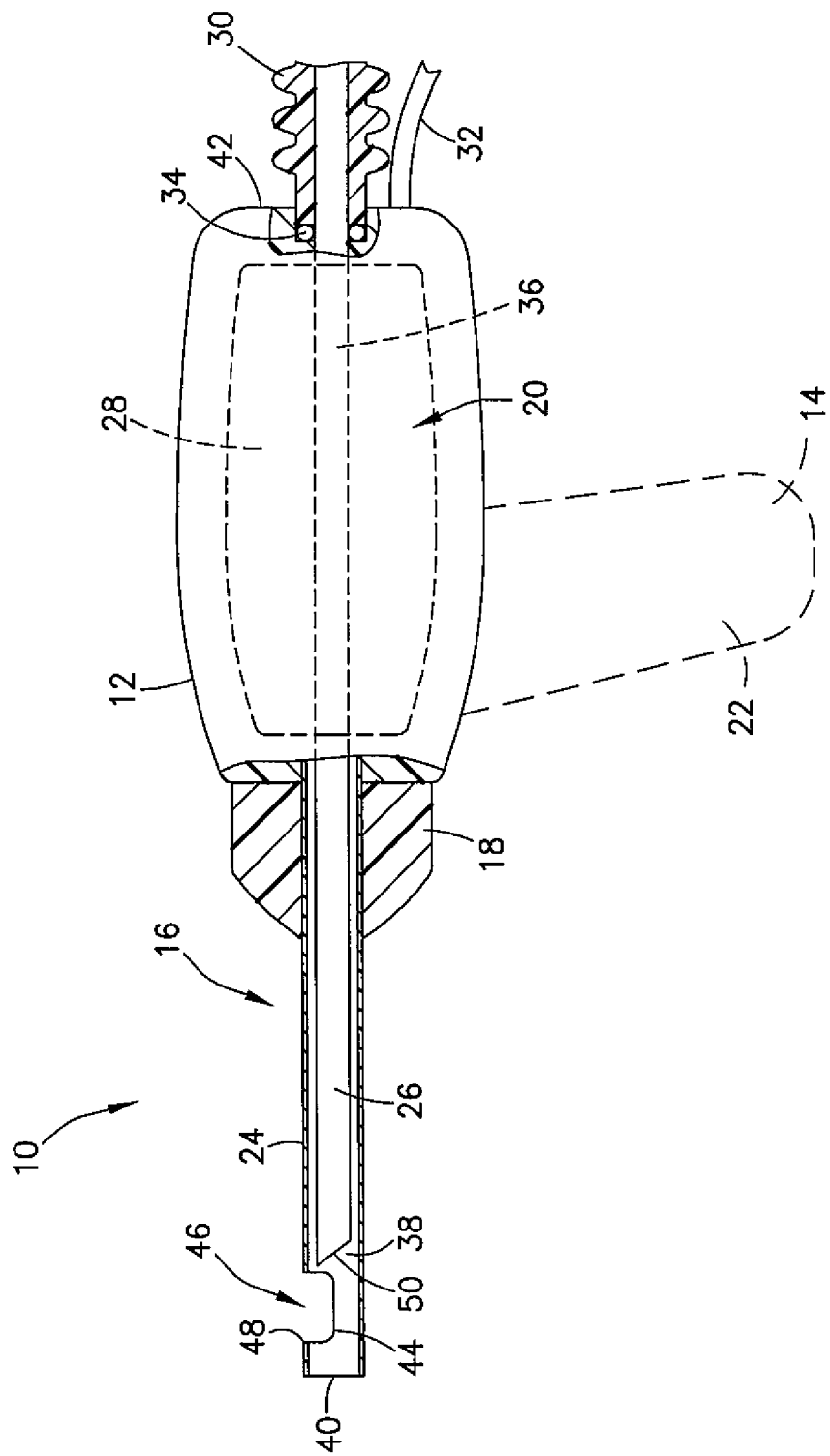
FIG. 1 is a side view of a medical device incorporating features of the invention.
Figure 3:
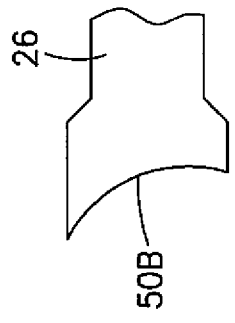
FIG. 3 is an alternate embodiment of a cutting tip used in the medical device shown in FIG. 1.
Figure 5:
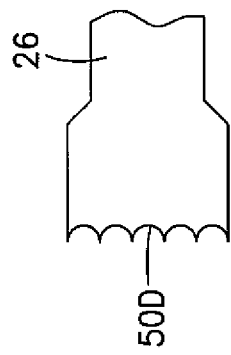
FIG. 5 is an alternate embodiment of a cutting tip used in the medical device shown in FIG. 1.
Figure 2:
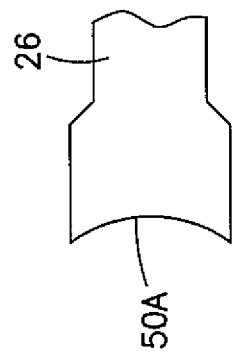
FIG. 2 is an alternate embodiment of a cutting tip used in the medical device shown in FIG. 1.
Figure 4:
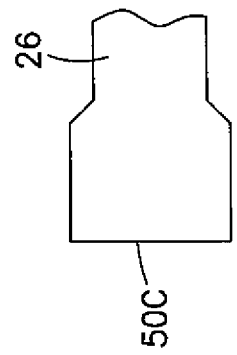
FIG. 4 is an alternate embodiment of a cutting tip used in the medical device shown in FIG. 1.

Referring to FIG. 1, there is shown a perspective view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

According to various exemplary embodiments, the medical device 10 is generally configured for use in the removal of nasal polyps, sub-mucosal debulk of turbinates, and functional endoscopic sinus surgery (FESS).

The medical device 10, which may be a disposable debrider for example, comprises a housing 12 (which may have a pistol grip portion 14), a blade tube section 16, and a nosepiece 18. The nosepiece 18 may be a rotatable nosepiece and is between the housing 12 and the blade tube section 16. However, it should be noted that exemplary embodiments of the medical device may comprise any suitable configuration such as configurations having a nosecone coupled to an outer member (of the housing), or any other suitable curved or straight debrider configuration which may comprise an irrigation feature, for example. The blade tube section 16 of the device 10 can be configured with large and small shaver tubes, depending on anatomy and surgeon preference, and can also be adapted for bipolar or monopolar radio-frequency (RF) power. An external ESG (electrosurgical generator) may supply the RF power, for example.

The housing 12 comprises an interior cavity 20 sized and shaped to house actuation members of the device 10. Additionally, in some embodiments the optional pistol grip portion 14 may include an interior cavity 22 which can also be sized and shaped to house actuation members (or other hardware) of the device 10.

The blade tube section 16 comprises an outer blade tube 24 and an inner blade tube 26, and the medical device 10 further comprises a blade drive system 28 mounted within the cavity 20 (or mounted within the cavity 22) which is configured to drive the inner blade tube 26. It should be noted that in some embodiments, the blade tubes 24, 26 may comprise flexible and/or curved tubes.

Additionally, the medical device 10 comprises a connector 30 and a power cable 32. The connector (or suction connection) 30 is configured to connect to a suction tube or a vacuum source. The connector 30 includes a dynamic seal 34 mounted inside of the connector 30. The dynamic seal 34 is configured to provide a sealed interface between the connector 30 and an inner lumen 36 (via the outer surface of the inner blade tube 26) of the inner blade tube 26. The power cable 32 is configured to provide power to components(s) of the blade drive system 28.

The outer blade tube 24 is (rotatably or fixedly) mounted to the housing 12 and acts as a static member. For example, according to various exemplary embodiments, the nosepiece 18 can be mounted to the outer blade tube 24 and can optionally rotate the outer blade tube 24 independent of the housing 12. The inner blade tube 26 is slidably mounted inside the outer blade tube (such that the inner blade tube 26 is slideably mounted within a lumen 38 of the outer blade tube 24).

The inner blade tube 26 is configured to be forced distally [i.e. towards the distal end 40] or proximally [i.e. towards the proximal end 42] by the blade drive system 28. The outer blade tube 24 comprises an opening 44 proximate the distal end 40 which forms a cutting window 46 for the medical device 10. The cutting window 46 is formed by a cutting edge 48 of the outer blade tube (i.e. the distal edge of the opening 44) and a cutting tip 50 of the inner blade tube 26. The reciprocal motion of the inner blade tube 26 provides for the cutting tip 50 to reciprocate relative to the cutting edge 48 to perform tissue cuts (i.e. by bringing the cutting tip 50 into alignment and out of alignment with the opening 44 of the outer blade tube 24). In the embodiment shown in FIG. 1, the cutting edge 48 is at the cylindrical face portion of the cutting window 46. However in alternate embodiments, the cutting edge may be provided at any suitable location along the distal end 40.

It should be noted that although various exemplary embodiments of the invention have been described in connection with the cutting tip 50 comprising an angled straight edge configuration, alternate embodiments may comprise other suitable configurations. For example, FIGS. 2-5 illustrate alternate embodiments for the cutting tip 50 (see cutting tips 50A, 50B, 50C, 50D).

Figure 6:
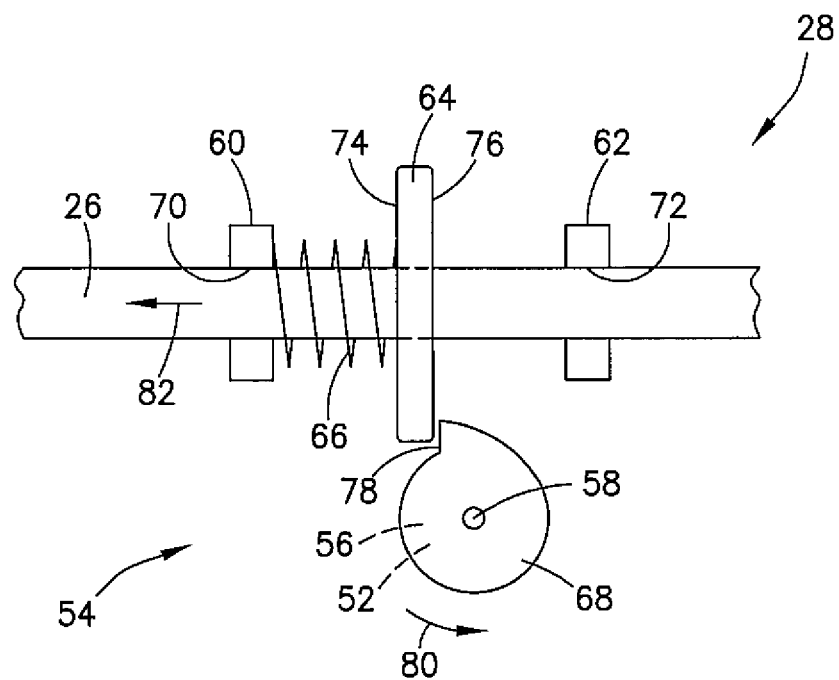
FIG. 6 is a top view of a blade drive system used in the medical device shown in FIG. 1.

Referring now also to FIG. 6, the blade drive system 28 comprises a motor 52 and a mechanical arrangement 54. The motor 52 is offset and substantially perpendicular relative to a central axis of the blade tube section 16. The motor 52 generally comprises a motor housing 56 and a motor shaft 58 extending from the motor housing 56. The motor shaft 58 is configured to rotate when the motor 52 is electrically energized (by power cable 32). According to some embodiments, the motor 52, or at least a portion of the motor 52, may be disposed within the grip cavity 22. However, in alternate embodiments, any suitable location for the motor 52 may be provided (such as the housing cavity 20, for example).

The mechanical arrangement 54 comprises a distal bushing 60, a proximal bushing 62, a collar 64, a spring 66, and a flywheel 68. The bushings 60, 62 are fixedly mounted to the housing 12 and each comprise an opening 70, 72 sized and shaped to allow reciprocation of the inner blade tube 26 therethrough. The collar 64 comprises a general flange shape and has a first side 74 and a second side 76 and is between the bushings 60, 62. The collar 64 is fixedly connected (or fixedly mounted) to the inner blade tube 26. The spring 66 is between the distal bushing 60 and the first side 74 of the collar 64.

According to various exemplary embodiments, the spring is a compression spring, however in alternate embodiments the spring may be an extension spring. Additionally, in some further embodiments, the spring may be between the proximate bushing 62 and the second side 76 of the collar 64.

The flywheel 68 comprises a cam portion 78. The cam portion 78 forms a projection on the rotating flywheel 68. The cam portion 78 is configured to make sliding contact with the second side 76 of the collar 64 (while the flywheel 68 is rotating) to impart motion to the inner blade tube 26 (through the collar 64 which is fixedly mounted to the inner blade tube 26).

Figure 7:
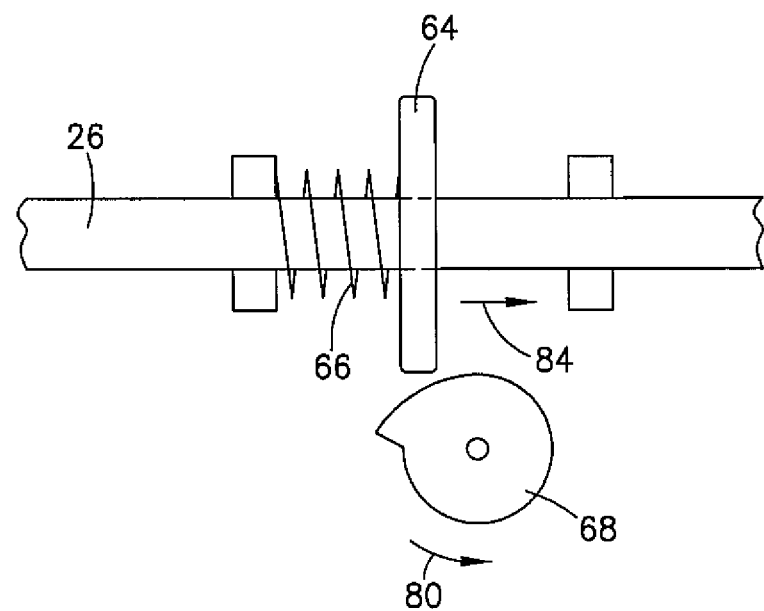
FIG. 7 is another top view of a blade drive system shown in FIG. 6.

The mechanical arrangement described above is configured to have the flywheel 68 (driven by the motor 52) rotate (see arrow 80) such that the cam portion (or cam shape) 78 interfaces with the collar 64. As the cam portion 78 rotates and engages the second side 76 of the collar 64, rotation of the flywheel 68 causes the cam portion 78 to push, or impart a force, in direction 82 to cause the collar 64 and the inner blade tube 26 to slide towards the distal end 40 (see FIG. 6). As the cam portion 78 moves past the collar 64 and disengages (see FIG. 7), the inner blade tube is returned to its home position (see arrow 84) due to a biasing force of the spring 66.

Although the embodiment above has been described in connection with a 'counter clockwise' rotation of the flywheel, alternate embodiments may be provided with a 'clockwise rotation' of the flywheel (with a corresponding cam portion) and the spring in the same location or with the spring between the collar 64 and the proximal bushing 62. In further embodiments, any suitable location(s) for the flywheel and/or spring which provide for reciprocal motion of the inner blade tube may be provided.

Figure 8:
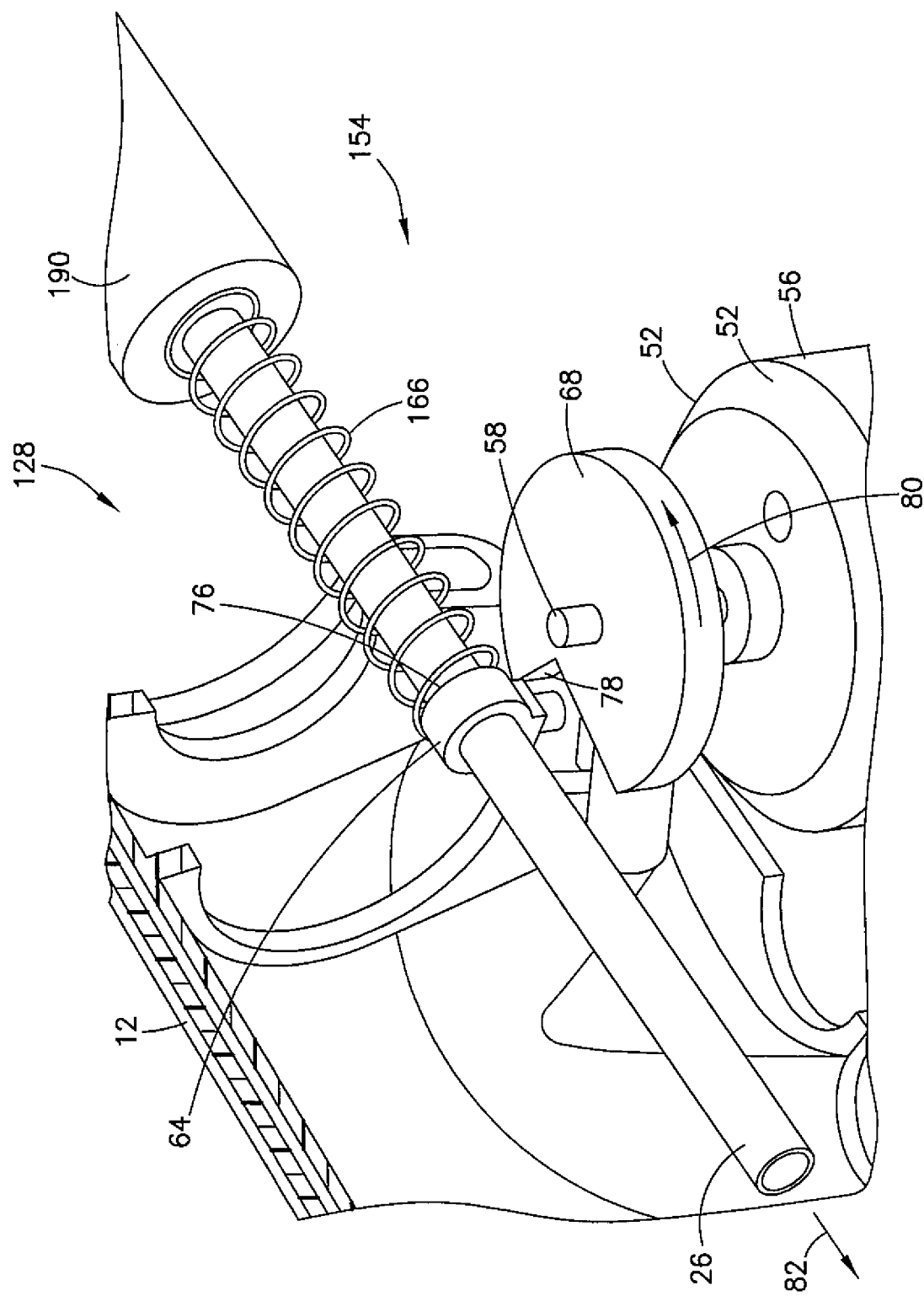
FIG. 8 is a perspective view of an alternate blade drive system used in the medical device shown in FIG. 1.

Referring now also to FIG. 8, an alternate embodiment of a blade drive system is shown. The blade drive system 128 is similar to the blade drive system 28 and similar features are similarly numbered. Similar to the mechanical arrangement 54, the mechanical arrangement 154 comprises a collar 64, a spring 166, and a flywheel 68. However, in this embodiment, the spring 166 is an extension spring connected between the collar 64 and a suction connector 190.

Similar to the blade drive system 28, the cam portion 78 is configured to make sliding contact with the second side 76 of the collar 64 (while the flywheel 68 is rotating) to impart motion to the inner blade tube 26 (through the collar 64 which is fixedly mounted to the inner blade tube 26). The mechanical arrangement 154 is configured to have the flywheel 68 (driven by the motor 52) rotate (see arrow 80) such that the cam portion (or cam shape) 78 interfaces with the collar 64. As the cam portion 78 rotates and engages the second side 76 of the collar 64, rotation of the flywheel 68 causes the cam portion 78 to push, or impart a force, in direction 82 to cause the collar 64 and the inner blade tube 26 to slide towards the distal end 40. As the cam portion 78 moves past the collar 64 and disengages, the inner blade tube is returned to its home position due to a biasing force of the extension spring 166. It should be noted that although this embodiment shows the spring 166 connected to the suction member 166, alternate embodiments may have the spring 166 connected to any other suitable fixed surface of e the device 10.

Technical effects of any one or more of the exemplary embodiments provide significant advantages over conventional configurations by providing greater force to the reciprocating blade than conventional air pressure-based devices can provide. A further technical effect of the various exemplary embodiments is providing a motor offset (and perpendicular) from a central axis of the blade tube section. Another technical effect of the various exemplary embodiments is that the blade is mounted with a spring in such a way that after each movement, the blade returns to its home position.

Figure 9:
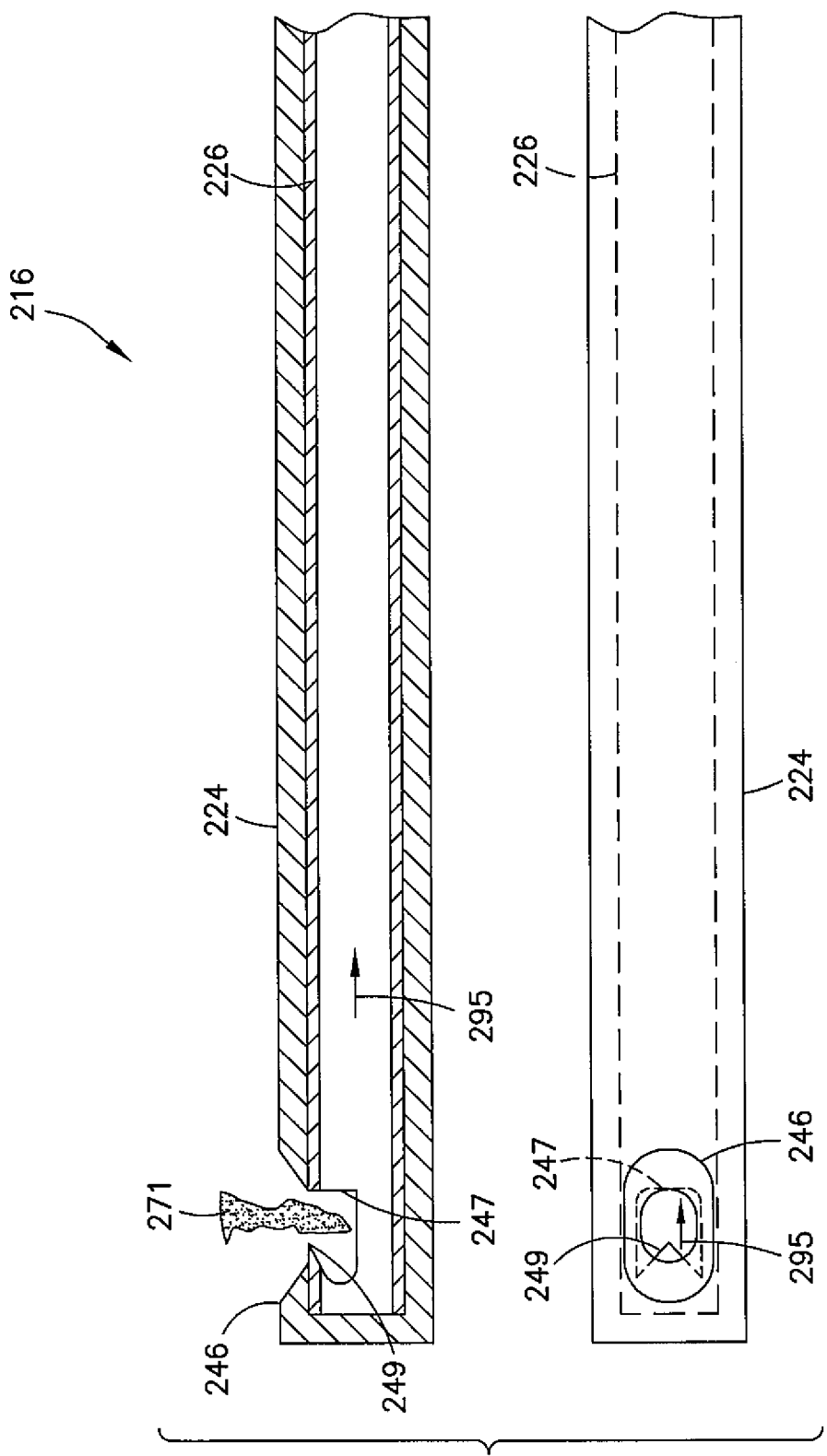
FIG. 9 is a section view and a top plan view of an alternate blade tube section used in the medical device shown in FIG. 1.

While various exemplary embodiments of the invention have been described in connection with a blade tube section 16 having a cutting edge 48 at the cutting window 46 of the outer blade tube 24, other configurations may be provided. For example, an alternate embodiment of a blade tube section is shown in FIG. 9 (illustrating a cross-section view [top] and a top plan view [bottom]). Similar to the blade tube section 16, the blade tube section 216 comprises an outer blade tube 224 and an inner blade tube 226 configured to be driven by the blade drive system 28. However in this embodiment, the inner blade tube 226 comprises a cutting window 247 and a cutting edge 249. The cutting window 247 is configured to be aligned with the window 246 of the outer blade tube 224 such that the cutting is provided when tissue 271 extends through the windows 246, 247 and a backwards motion of the inner blade tube 226 (towards the proximate end [see arrow 295]) causes the cutting edge 249 to cut through the tissue 271.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device comprising: a blade tube section comprising an outer blade tube, an inner blade tube, and a cutting window at a distal end of the blade tube section; a motor offset from a central axis of the blade tube section; and a mechanical arrangement between the inner blade tube and the motor.

A medical device as above, further comprising a collar connected to the inner tube member.

A medical device as above, wherein the mechanical arrangement comprises a flywheel, wherein the flywheel is connected to the motor.

A medical device as above, wherein flywheel comprises a cam portion.

A medical device as above, wherein the cam portion is configured to engage the collar.

A medical device as above, wherein the motor comprises a motor shaft, wherein the motor shaft is substantially perpendicular to the central axis of the blade tube section.

A medical device as above, further comprising a collar, a bushing, and a spring, wherein the collar is connected to the inner tube member, and wherein the spring is between the bushing and the collar.

A medical device as above, wherein the inner blade tube is configured to reciprocate relative to the outer blade tube.

In another exemplary embodiment, a medical device comprising: a blade tube section comprising an outer blade tube, and inner blade tube, and a cutting window at a distal end of the blade tube section; a motor; and a cam portion between the inner blade tube and the motor.

A medical device as above, further comprising a collar fixedly connected to the inner tube member.

A medical device as above, wherein a mechanical arrangement is between the inner blade tube and the motor.

A medical device as above, wherein the mechanical arrangement comprises a flywheel, wherein the flywheel is connected to the motor.

A medical device as above, wherein flywheel comprises a cam portion.

A medical device as above, wherein the cam portion is configured to contact a member on the inner blade tube.

A medical device as above, further comprising a collar, a bushing, and a spring, wherein the collar is connected to the inner tube member, and wherein the spring is between the bushing and the collar.

A medical device as above, wherein the inner blade tube is configured to reciprocate relative to the outer blade tube.

A medical device as above, wherein the motor is substantially perpendicular from a central axis of the blade tube section.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
   a blade tube section extending along a longitudinal axis and comprising an outer blade tube, an inner blade tube slidably mounted within the outer blade tube, and a cutting window at a distal end of the blade tube section;
   a motor offset from the longitudinal axis of the blade tube section;
   a collar extending from and fixedly connected to an outer surface of the inner blade tube, the collar including a distal face oriented toward the distal end of the blade tube section and an opposing proximal face oriented toward a proximal end of the blade tube section; and
   a mechanical arrangement between the inner blade tube and the motor, the mechanical arrangement comprising a rotatable flywheel connected to the motor, the flywheel including a cam portion configured to make sliding contact with the proximal face of the collar, as the flywheel rotates, to push the collar and the attached inner blade tube in a distal direction along the longitudinal axis.

2. The medical device of claim 1 wherein the motor comprises a motor shaft, wherein the motor shaft is substantially perpendicular to the longitudinal axis of the blade tube section.

3. The medical device of claim 1 further comprising a bushing and a spring, wherein the spring is between the bushing and the collar.

4. The medical device of claim 1 wherein the inner blade tube is configured to reciprocate relative to the outer blade tube.

5. A medical device comprising:
   a housing;
   a blade tube section extending from the housing and comprising an outer blade tube, an inner blade tube, and a cutting window at a distal end of the blade tube section, wherein the inner blade tube is configured to reciprocate relative to the outer blade tube;
   a collar fixedly connected to the inner blade tube;
   a bushing including an opening sized and shaped to allow reciprocation of the inner blade tube therethrough;
   a motor disposed within the housing and substantially perpendicular to a central axis of the blade tube section;
   a cam portion between the inner blade tube and the motor; and
   a spring configured to provide a bias force sufficient to move the inner blade tube from a first position to a second position, wherein the spring extends between and is in contact with the collar and the bushing.

6. The medical device of claim 5 wherein a mechanical arrangement is between the inner blade tube and the motor.

7. The medical device of claim 6 wherein the mechanical arrangement comprises a flywheel, wherein the flywheel is connected to the motor.

8. The medical device of claim 7 wherein the cam portion is located on the flywheel.

9. The medical device of claim 8 wherein the cam portion is configured to contact a member on the inner blade tube.

10. A medical device comprising:
a blade tube section extending along a longitudinal axis and comprising an outer blade tube, an inner blade tube, and a cutting window at a distal end of the blade tube section;
a rotary motor offset from a central axis of the blade tube section;
a collar extending from and fixedly connected to an outer surface of the inner blade tube; and
a rotatable flywheel connected to an output of the motor, the flywheel including a cam portion that selectively engages the collar to drive reciprocating motion of the inner blade tube between a first axial position and a second axial position by pushing the collar and the attached inner blade tube in a distal direction along the longitudinal axis.

* * * * *